United States Patent
Anderson (10) Patent No.: US 7,862,599 B2
(45) Date of Patent: Jan. 4, 2011

(54) CONVECTIVE WARMING DEVICE WITH A DRAPE

(75) Inventor: Thomas P. Anderson, Savage, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 1017 days.

(21) Appl. No.: 11/656,777

(22) Filed: Jan. 23, 2007

(65) Prior Publication Data

US 2008/0177361 A1     Jul. 24, 2008

(51) Int. Cl.
*A61F 7/00* (2006.01)
(52) U.S. Cl. ..................... 607/104; 607/108
(58) Field of Classification Search ........... 607/96, 607/104, 107, 108
See application file for complete search history.

(56) References Cited

U.S. PATENT DOCUMENTS

| | | | |
|---|---|---|---|
| 2,512,559 A | 6/1950 | Williams | 5/347 |
| 2,573,414 A | 10/1951 | Dunn | 128/144 |
| 2,826,758 A | 3/1958 | Kahn | 2/81 |
| 3,468,299 A | 9/1969 | D'Amato | 126/204 |
| 3,610,323 A | 10/1971 | Troyer | 165/46 |
| 3,757,366 A | 9/1973 | Sacher | 5/347 |
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |
| 4,146,933 A | 4/1979 | Jenkins et al. | 2/2 |
| 4,369,528 A | 1/1983 | Vest et al. | 2/69 |
| 4,494,248 A | 1/1985 | Holder | 2/69 |
| 4,524,463 A | 6/1985 | Ogden | 2/105 |
| 4,558,468 A | 12/1985 | Landry et al. | 2/51 |
| 4,578,825 A | 4/1986 | Vote | 2/114 |
| 4,587,671 A | 5/1986 | Rodriguez, Jr. et al. | 2/69 |
| 4,651,727 A | 3/1987 | Howorth | 128/201.23 |
| 4,653,120 A | 3/1987 | Leaf | 2/114 |
| 4,696,066 A | 9/1987 | Ball et al. | 2/272 |
| 4,718,124 A | 1/1988 | Sawicki et al. | 2/114 |
| 4,777,802 A | 10/1988 | Feher | 62/3 |
| 4,787,101 A | 11/1988 | Feinberg | 2/105 |
| 4,914,752 A | 4/1990 | Hinson et al. | 2/2 |

(Continued)

FOREIGN PATENT DOCUMENTS

FR        821150        11/1937

(Continued)

OTHER PUBLICATIONS

EPO Examination Report mailed Dec. 17, 2007, in EPO3719690.4-1526, EP Regional Phase of PCT/US2003/11128 (published as WO/2003/086500).

(Continued)

*Primary Examiner*—Roy D Gibson
(74) *Attorney, Agent, or Firm*—Terrance A. Meador; INCAPLAW (57) ABSTRACT

A convective warming device including a clinical garment and at least one inflatable convective apparatus supported on an inside surface of the garment is provided with a drape. When the convective warming device is used to warm a person, the drape is deployed over skin of the person not covered by the clinical garment. The drape protects the covered skin from thermal injury by an air hose used to conduct heated pressurized air to the inflatable convective apparatus.

29 Claims, 6 Drawing Sheets

U.S. PATENT DOCUMENTS

| | | | |
|---|---|---|---|
| 4,964,282 A | 10/1990 | Wagner | 62/259.3 |
| 5,062,424 A | 11/1991 | Hooker | 128/379 |
| 5,184,612 A | 2/1993 | Augustine | 128/400 |
| 5,190,031 A | 3/1993 | Guibert et al. | 128/399 |
| 5,255,390 A | 10/1993 | Gross et al. | 2/2 |
| 5,304,213 A | 4/1994 | Berke et al. | 607/107 |
| 5,360,439 A | 11/1994 | Dickerhoff et al. | 607/107 |
| 5,367,710 A | 11/1994 | Karmin | 2/114 |
| 5,411,541 A | 5/1995 | Bell et al. | 607/104 |
| 5,443,488 A | 8/1995 | Namenye et al. | 607/107 |
| 5,572,742 A | 11/1996 | McFadden | 2/114 |
| 5,575,006 A | 11/1996 | Wolfe | 2/114 |
| 5,611,087 A | 3/1997 | Adkins | 2/114 |
| 5,620,482 A | 4/1997 | Augustine et al. | 607/107 |
| 5,697,963 A | 12/1997 | Augustine | 607/108 |
| 5,733,318 A | 3/1998 | Augustine | 607/104 |
| 5,749,109 A | 5/1998 | Kappel | 5/423 |
| 5,785,716 A | 7/1998 | Bayron | 607/108 |
| 5,891,187 A | 4/1999 | Winthrop et al. | 607/96 |
| 5,941,907 A | 8/1999 | Augustine | 607/107 |
| 5,946,722 A | 9/1999 | Trautmann | 2/83 |
| 5,970,519 A | 10/1999 | Weber | 2/81 |
| 5,974,605 A | 11/1999 | Dickerhoff et al. | 5/421 |
| 6,049,907 A | 4/2000 | Palomo | 2/51 |
| 6,154,883 A | 12/2000 | Spann et al. | 2/69 |
| 6,156,058 A | 12/2000 | Kappel et al. | 607/107 |
| 6,203,567 B1 | 3/2001 | Augustine | 607/104 |
| 6,216,270 B1 | 4/2001 | Moquin et al. | 2/69 |
| 6,235,659 B1 | 5/2001 | McAmish et al. | 442/79 |
| 6,378,136 B2 | 4/2002 | Matsushita | 2/114 |
| 6,484,321 B1 | 11/2002 | Shamam | 2/114 |
| 6,511,501 B1 | 1/2003 | Augustine et al. | 607/96 |
| 6,524,332 B1 | 2/2003 | Augustine et al. | 607/107 |
| 6,551,347 B1 | 4/2003 | Elkins | 607/104 |
| 6,571,574 B1 | 6/2003 | Blackstone | 62/420 |
| 6,596,019 B2 | 7/2003 | Turner et al. | 607/108 |
| 6,647,552 B1 | 11/2003 | Hogan | 2/114 |
| 6,694,522 B1 | 2/2004 | Neal | 2/114 |
| 6,792,622 B2 | 9/2004 | Graves | 2/114 |
| 6,799,332 B2 | 10/2004 | Hatton | 2/114 |
| 6,820,622 B1 | 11/2004 | Teves et al. | 128/849 |
| 6,851,125 B2 | 2/2005 | Fujikawa et al. | 2/51 |
| 6,876,884 B2 | 4/2005 | Hansen et al. | 607/98 |
| 7,001,416 B2 | 2/2006 | Augustine et al. | 607/104 |
| 7,226,454 B2 | 6/2007 | Albrecht et al. | 607/104 |
| 7,276,076 B2 | 10/2007 | Bieberich | 607/108 |
| 7,364,584 B2 | 4/2008 | Anderson | 607/107 |
| 7,470,280 B2 | 12/2008 | Bieberich | 607/104 |
| 2003/0126668 A1 | 7/2003 | Scroggins | 2/114 |
| 2005/0015127 A1 | 1/2005 | Bieberich | 607/104 |
| 2005/0143796 A1 | 6/2005 | Augustine et al. | 607/104 |
| 2006/0047332 A1 | 3/2006 | Malmberg et al. | 607/104 |
| 2006/0122671 A1 | 6/2006 | Albrecht et al. | 607/104 |
| 2006/0122672 A1 | 6/2006 | Anderson | 607/104 |
| 2006/0147320 A1 | 7/2006 | Hansen et al. | 417/313 |
| 2006/0184216 A1 | 8/2006 | Van Duren | 607/104 |
| 2006/0184217 A1 | 8/2006 | Van Duren | 607/104 |
| 2006/0184218 A1 | 8/2006 | Bieberich | 607/104 |
| 2006/0259104 A1 | 11/2006 | Panser et al. | 607/104 |
| 2007/0093882 A1 | 4/2007 | Anderson et al. | 607/104 |
| 2007/0093883 A1 | 4/2007 | Anderson et al. | 607/104 |
| 2007/0093884 A1 | 4/2007 | Anderson et al. | 607/104 |
| 2007/0093885 A1 | 4/2007 | Anderson et al. | 607/104 |
| 2007/0239239 A1 | 10/2007 | Albrecht et al. | 607/96 |
| 2008/0027521 A1 | 1/2008 | Bieberich | 607/96 |
| 2008/0027522 A1 | 1/2008 | Bieberich | 607/96 |
| 2008/0125840 A1 | 5/2008 | Anderson | 607/96 |
| 2008/0177361 A1 | 7/2008 | Anderson | 607/108 |
| 2009/0062891 A1 | 3/2009 | Bieberich | 607/104 |
| 2009/0149931 A9 | 6/2009 | Anderson | 607/104 |
| 2009/0228083 A1 | 9/2009 | Anderson et al. | 607/107 |

FOREIGN PATENT DOCUMENTS

| | | |
|---|---|---|
| GB | 475811 | 11/1937 |
| GB | 1 462 033 | 1/1997 |
| SE | 525 415 | 2/2005 |
| WO | WO 97/14381 A1 | 4/1997 |
| WO | WO 98/48652 | 11/1998 |
| WO | WO 00/62726 | 10/2000 |
| WO | WO 03/086500 A3 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2007/047917 A1 | 4/2007 |
| WO | WO 2008/013603 | 1/2008 |
| WO | WO 2008/091486 | 7/2008 |

OTHER PUBLICATIONS

EPO Examination Report mailed Sep. 2, 2008, in EP05789978.3, EP Regional Phase of PCT/US2005/025355 (published as WO/2006/020170).
EPO Examination Report mailed Jan. 23, 2009, in EP05853202, EP Regional Phase of PCT/US2005/044214 (published as WO/2006/063027).
P.O. Fanger, Thermal Comfort: Analysis and Applications in Environmental Engineering, Danish Technical Press, 1970, pp. 5-67.
C.B. Mahony & J. Odom, Maintaining intraoperative normothermia: A meta-analysis of outcomes with costs. *AANA Journal*. Apr. 1999. v. 67, No. 2:155-164.
Porta-Chill—The Portable Air-Chiller—Brochure, http://www.portachil.com/, Dec. 3, 2002.
EPO Examination Report mailed Oct. 24, 2006, in EP03719690.4-1526, EP Regional Phase of PCT/US2003/11128 (published as WO/2003/086500).
International Search Report in PCT/US2006/004644, mailed Dec. 18, 2006.
Written Opinion of the International Searching Authority (EPO) in PCT/US2006/004644, mailed Dec. 18, 2006.
EPO Examination Report mailed Jan. 8, 2008, in EP05853005.6, EP Regional Phase of PCT/US2005/043968 (published as WO/2006/062910).
EPO Examination Report mailed Apr. 24, 2009, in EP06826351.6, EP Regional Phase of PCT/US2006/041028 (published as WO/2007/047917).
EPO Examination Report mailed Jun. 22, 2009, in EP05853202.9, EP Regional Phase of PCT/US2005/043968 (published as WO/2006/062910).
EPO Examination Report mailed Sep. 3, 2009 in EP 07795671.2, EP Regional Phase of PCT/US2007/013073 (published as WO/2008/013603).
EPO Examination Report mailed Sep. 29, 2009, in EP06720577.3, EP Regional Phase of PCT/US2006/004644 (published as WO/2006/086587).
EPO Examination Report mailed Nov. 10, 2009, in EP08705485.4, EP Regional Phase of PCT/US2008/000141 (published as WO/2008/091486).
Applicants' response to the Examination Report in EP08705485.4, mailed Mar. 9, 2010.
EPO Examination Report mailed Apr. 14, 2010 in EP06826351.6, EP Regional Phase of PCT/US2006/041028 (published as WO/2007/047917).
Written Opinion of the International Search Authority (EPO) in PCT/US2006/041028, mailed Feb. 20, 2007.
International Search Report and Written Opinion in PCT/US2005/025355, mailed Dec. 1, 2005.
International Search Report and Written Opinion in PCT/US2005/043968, mailed Apr. 19, 2006.

International Search Report and Written Opinion in PCT/US2005/044214, mailed Apr. 19, 2006.
International Search Report and Written Opinion in PCT/US2006/041028, mailed Feb. 20, 2007.
International Search Report and Written Opinion in PCT/US2008/000141, mailed Nov. 11, 2008.
International Search Report and Written Opinion in PCT/US2007/013073, mailed Nov. 9, 2007.

CONVECTIVE WARMING DEVICE WITH A DRAPE

CROSS REFERENCE TO RELATED APPLICATIONS

This application contains subject matter related to the subject matter of the following patent applications, all commonly owned herewith:

Patent Cooperation Treaty (PCT) Application No. PCT/US2003/11128, filed Apr. 10, 2003, entitled "Patient Comfort Apparatus and System", and published on Oct. 23, 2003 under Publication No. WO 2003/086500;

PCT Application No. PCT/US2005/025355, filed Jul. 18, 2005, entitled "Perioperative Warming Device", and published on Feb. 23, 2006 under Publication No. WO 2006/020170;

PCT Application No. PCT/US2005/043968, filed Dec. 6, 2005, entitled "Warming Device with Varied Permeability", and published on Jun. 15, 2006 under Publication No. WO 2006/062910;

PCT Application No. PCT/US2005/044214, filed Dec. 6, 2005, entitled "Warming Device", and published on Jun. 15, 2006 under Publication No. WO 2006/063027;

PCT Application No. PCT/US2006/004644, filed Feb. 9, 2006, entitled "Warming Device for Perioperative Use", and published on Aug. 17, 2006 under Publication No. WO2006/086587;

PCT Application No. PCT/US2006/41028, filed Oct. 19, 2006, entitled "Multifunction Warming Device for Perioperative Use";

U.S. patent application Ser. No. 10/411,865, filed Apr. 10, 2003, entitled "Patient Comfort Apparatus and System", and published on Oct. 16, 2003 under Publication No. US 2003/0195596, now U.S. Pat. No. 7,001,416;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 10/508,319, filed Sep. 20, 2004, entitled "Patient Comfort Apparatus and System", and published on Jun. 30, 2005 under Publication No. US 2005/0143796;

U.S. patent application Ser. No. 11/005,883, filed Dec. 7, 2004, entitled "Warming Device with Varied Permeability", and published on Jun. 8, 2006 under Publication No. US 2006/0122671;

U.S. patent application Ser. No. 11/006,491, filed Dec. 7, 2004, entitled "Warming Device", and published on Jun. 8, 2006 under Publication No. US 2006/0122672;

U.S. patent application Ser. No. 11/057,396, filed Feb. 11, 2005, entitled "Perioperative Warming Device", and published on Aug. 17, 2006 under Publication No. US2006/0184215;

U.S. patent application Ser. No. 11/057,397, filed Feb. 11, 2005, entitled "Thermal Blanket for Warming the Limbs", and published on Aug. 17, 2006 under Publication No. US 2006/0184216;

U.S. patent application Ser. No. 11/057,403, filed Feb. 11, 2005, entitled "Warming Device for Perioperative Use", and published on Aug. 17, 2006 under Publication No. US 2006/0184217;

U.S. patent application Ser. No. 11/057,404, filed Feb. 11, 2005, entitled "Clinical Garment for Comfort Warming and Prewarming", and published on Aug. 17, 2006 under Publication No. US 2006/0184218;

U.S. patent application Ser. No. 11/260,706, filed Oct. 27, 2005, entitled "Patient Comfort Apparatus and System", and published on Mar. 9, 2006 under Publication No. US 2006/0052853;

U.S. patent application Ser. No. 11/363,136, filed Feb. 27, 2006, entitled "Forced Air Warming Unit", and published on Jul. 6, 2006 under Publication No. US 2006/0147320;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/583,432, filed Oct. 19, 2006, entitled "Multifunction Warming Device for Perioperative Use";

U.S. patent application Ser. No. 11/583,477, filed Oct. 19, 2006, entitled "Multifunction Warming Device with Provision for Being Secured";

U.S. patent application Ser. No. 11/583,480, filed Oct. 19, 2006, entitled "Multifunction Warming Device with Provision for Warming Hands"; and U.S. patent application Ser. No. 11/583,481, filed Oct. 19, 2006, entitled "Multifunction Warming Device with an Upper Body Convective Apparatus".

BACKGROUND

The field concerns devices that warm a person convectively. Particularly, the field concerns warming devices constituted of a clinical garment, one or more inflatable convective apparatuses inside the garment, and a drape.

Use of the term "convective" to denote the transfer of heat to a person refers to the principal mode of heat transfer, it being understood that heat may at the same time be transferred between a convective device and a body by conduction and radiation, although not to the degree of convection.

The patent applications referenced above describe warming devices constituted of a clinical garment and one or more convective apparatuses supported on an inside surface of the garment. Arizant Healthcare Inc., the assignee of this and the cross-referenced applications, makes and sells such devices under its BAIR PAWS® brand. In this regard, see the website at bairpaws.com.

The convective warming devices described in the referenced patent applications, and other similar convective warming devices include a clinical garment worn by or otherwise disposed on or over a patient. Because it may be easily moved and adjusted while being worn, or removed and put back on, the clinical garment affords mobility for users and provides convenience for clinicians.

A warming device as described in the referenced patent applications includes at least one convective apparatus attached to, or formed integrally on, an inside surface of a clinical garment, where it receives a stream of pressurized, heated air, inflates in response to the pressurized air, distributes the heated air, and emits the heated air through one or more permeable surfaces. The heated air is emitted inside the clinical garment. Depending on the structure of the convective apparatus, the warming device may be operated to maintain the comfort of a user wearing the clinical garment, or to warm the user for therapeutic purposes (such as treatment of hypothermia). Further, a convective apparatus can be constructed with multiple, separately inflatable sections so that a warming device may be operated to provide comfort warming by inflating one section and/or therapeutic warming by inflating another section.

To operate a convective warming device described in the referenced patent applications, a forced air warming unit is connected to an inlet port of an inflatable convective apparatus by means of an air hose. The forced air warming unit heats and pressurizes air, and the air hose conducts the stream of heated pressurized air to the inlet port. Heated air flowing into the inlet port inflates the apparatus, and also heats the air hose. Prolonged contact with the heated air hose can cause thermal injury to the skin of a user not covered by the clinical garment. Such contact may occur, for example, if the clinical garment, when worn, is of a length that reaches the knees of a user. In this regard, presume a convective warming device is deployed for use on a prone surgical patient, and an air hose runs between a forced air warming unit near the patient's feet. If the air hose rests on the skin of one or both of the patient's shins and/or feet for the duration of surgery, deep thermal injury to the skin caused by the pressure and heat of the air hose can result.

The risk of thermal injury caused by a hot air hose during use of a convective warming device may be mitigated or prevented by deploying a drape from the clinical garment over exposed skin so that the air hose lies on the drape instead of the skin covered by the drape.

SUMMARY

A convective warming device including a clinical garment and at least one convective apparatus supported on an inside surface of the garment is provided with a drape. The convective apparatus receives and distributes heated pressurized air and then circulates the distributed air through permeable surface areas to warm a patient covered by the clinical garment. The drape may be deployed from the clinical garment over skin not covered by the garment.

DETAILED DESCRIPTION

A convective warming device is constituted of a clinical garment and an inflatable convective apparatus supported on an inside surface of the garment. In this regard, a "clinical garment" is a robe-like article used to clothe a patient in a clinical setting. The clinical garment has an open bottom like a skirt or kilt and is supported primarily at the shoulders and/or neck of a user. This definition of clinical garment includes hospital gowns, robes, bibs, and other equivalents. The clinical setting may be a medical or dental office or clinic, a hospital, or any facility or institution that provides medical or dental treatment to patients. Preferably, although not necessarily, the clinical garment opens at the back or on a side. An inflatable convective apparatus is an article that receives and distributes at least one stream of heated pressurized air, and inflates and emits the heated air through one or more permeable surfaces. An inflatable convective apparatus may have one inflatable section, or it may have two or more separately inflatable sections. In some aspects, a convective warming device may include more than one inflatable convective apparatus. When a convective warming device is used to warm a person, an inflatable convective apparatus is positioned by the clinical garment to be disposed on, adjacent, or next to the core and/or the limbs of the person's body when the clinical garment is worn by or otherwise disposed on the person.

In one aspect, a convective warming device may be worn on a person where it receives a stream of heated pressurized air, distributes the pressurized air within a convective apparatus, and emits the air through one or more surfaces of the convective apparatus to warm the person's body for comfort or therapy.

The convective apparatuses illustrated and discussed below are inflatable, and their structures, flaccid when not inflated, tauten when receiving a stream of pressurized air.

A representative convective warming device is shown the figures and described in this specification only to provide a basis for explaining and illustrating the structure and use of several drape embodiments. In fact, any of the drape embodiments, or any equivalent thereof, may be used with any convective warming device constituted of a clinical gown and at least one inflatable convective device supported on an inside surface thereof.

Figure 1:
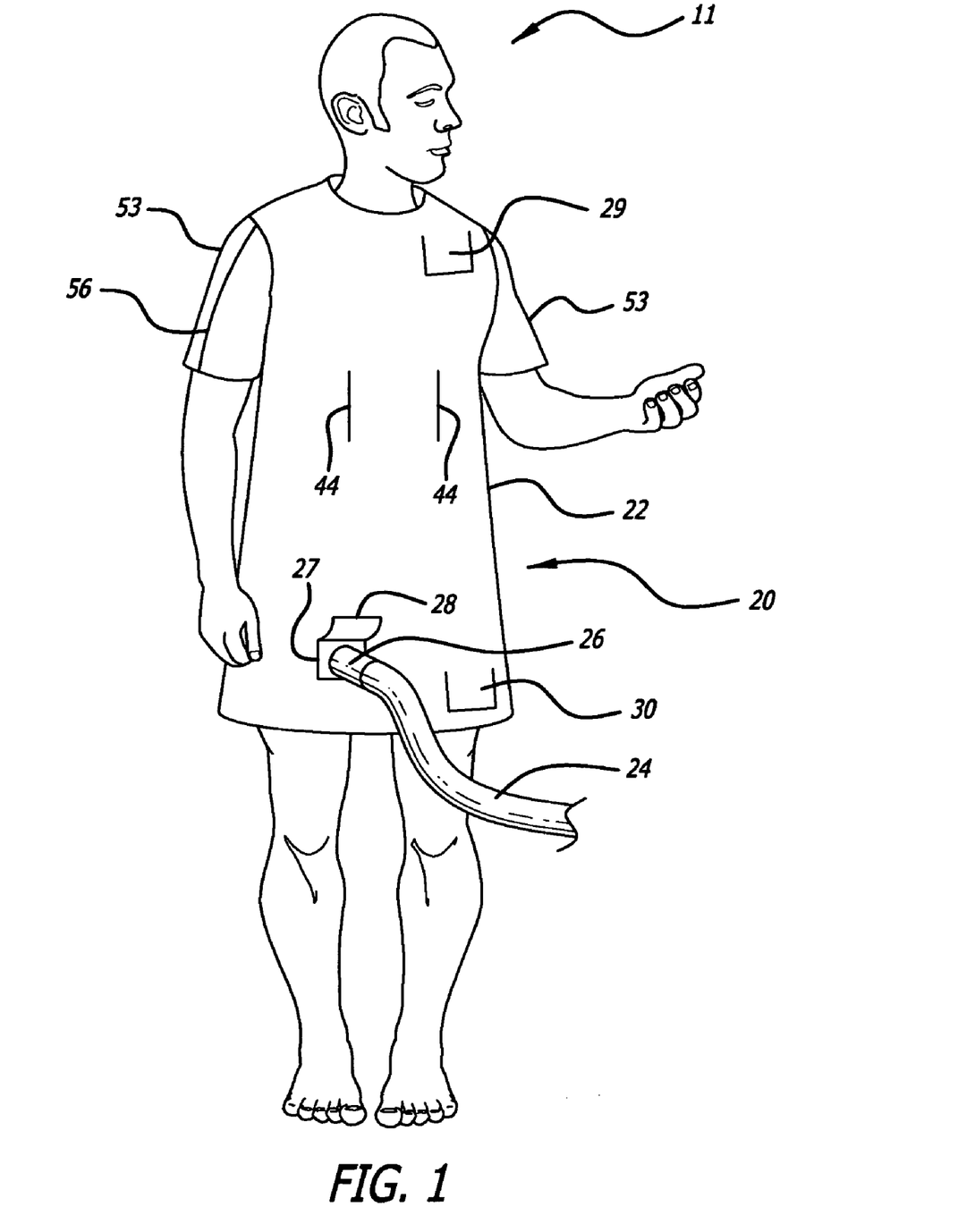
FIG. 1 is an illustration of a person wearing a convective warming device.

Refer now to the figures in which a person 11 wearing a representative convective warming device 20 is illustrated in FIG. 1. The convective warming device 20 is constituted of a clinical garment 22 and one or more convective apparatuses (not seen in this view) supported on an inside surface of the clinical garment 22. An inflatable convective apparatus is operated by provision of heated, pressurized air from a forced air warming unit (not seen in this view) through an air hose with a nozzle that is received in an inlet port of the convective apparatus. One such air hose 24, with a nozzle 26, is shown in FIG. 1, and an inlet port is indicated by reference numeral 27 in FIG. 1. The inlet port 27 is accessed through a flap 28 in the clinical garment 22. In some aspects, other convective apparatus inlet ports may be provided and accessed through other flaps in the clinical garment 22 such as flaps 29 and 30.

Figure 2:
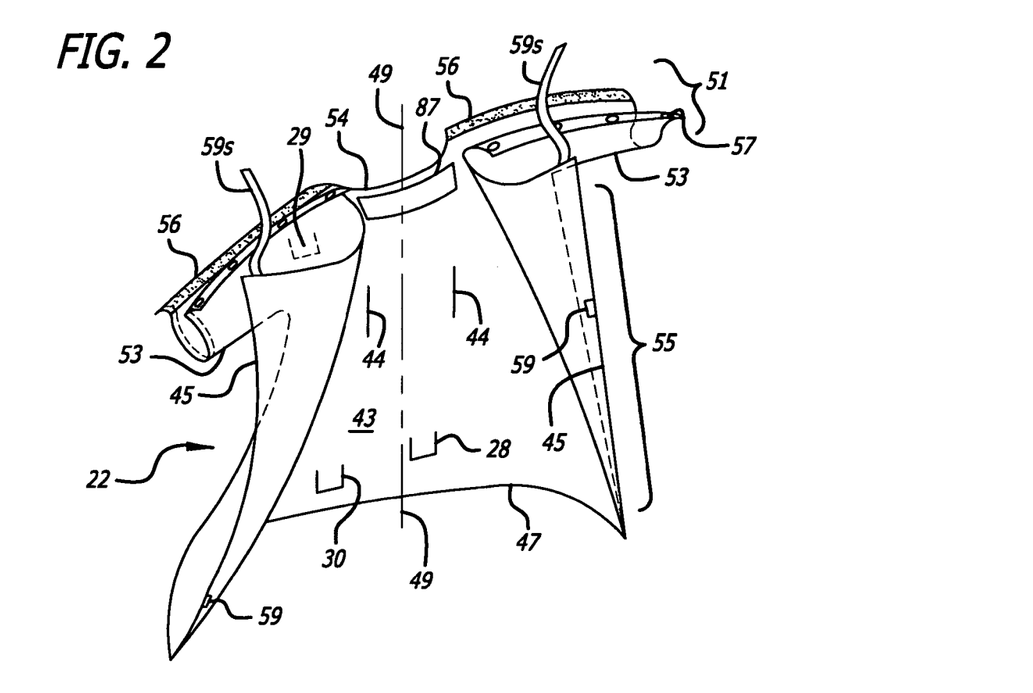
FIG. 2 is a perspective view to the rear of a clinical garment, with the clinical garment partially opened to show an inside surface that supports at least one convective apparatus.

FIG. 2 is a perspective view from the rear of a representative construction of the clinical garment 22, looking toward an inside surface of the garment. This construction is for illustration only; in fact other clinical gown constructions may also be adapted for any of the drape embodiments to be described, or any equivalent thereof.

With reference to FIGS. 1 and 2, the clinical garment 22 includes the inside surface 43, which faces the chest or thorax of a person wearing the garment, and which supports one or more convective apparatuses. The clinical garment 22 further includes two opposing lateral edges or hems 45, a lower edge or hem 47, and a longitudinal axis 49. Two slits 44 may be provided through the front of the clinical garment. The clinical garment 22 has an upper portion 51 with two opposing sleeves 53 and a scooped upper edge 54, and a lower portion 55. The flaps 28, 29, and 30 that provide access to inlet ports through the front of the garment 22 are also visible in FIG. 2. The sleeves 53 may be long or short. Short sleeves are preferred if access must be had to a person's arms for instrumentation and/or IV delivery. Each sleeve 53 includes an elongate seam 56 (both seen closed in FIG. 1). Each seam 56 may be held closed by means 57 including, for example, buttons, snaps, hook and loop material, tape, and/or straps, or any equivalent thereof. Such means can be operated to let a seam be opened and to again close the seam, once opened. The clinical garment 22 may open on a side. Preferably, the clinical garment 22 opens in the rear. The opening may be full, as illustrated in FIG. 2, or it may be partial, such as a slit rising from the lower hem 47. As per the example shown in FIG. 2, the opening may be closed by means 59 along the lateral hems 45 which releasably connect to keep the hems together. Such means may include buttons, snaps, hook and loop material, tape, and/or straps, and/or any equivalent thereof. In keeping with the example of FIG. 2, if straps are used to close the opening, the straps may be attached to the clinical garment 22, or formed integrally therewith as a step in manufacturing the clinical garment 22. For example only, two integrally-formed straps 59s for tying the opposing lateral hems 45 together in the upper portion 51 are seen in FIG. 2. Additional opposing straps may be attached to the outside surface of the clinical garment 22 with enough reach to be tied together around the outside of the clinical garment, near its middle. With enough overlap of the lateral hems 45, the opening in the clinical garment 22 can be completely closed and secured, with the lateral hems overlapping to afford concealment of a patient's private parts. The clinical garment 22 may be constructed from nonwoven or woven materials. Preferably, the clinical garment 22 is made from a nonwoven blend of spunlace polyester and wood pulp.

Figure 3:
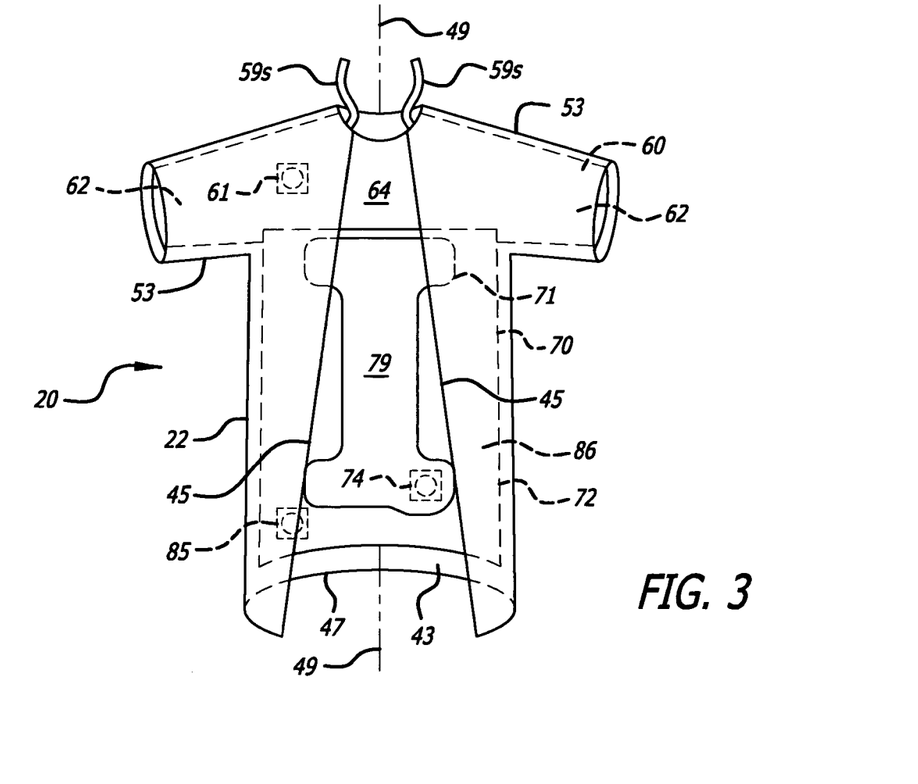
FIG. 3 is a rear elevation view of a convective warming device with two convective apparatuses.

FIG. 3 is an elevation view of the convective warming device 20, shown from the rear with the clinical garment 22 partially opened. When a drape is included, the device 20 may include one or more inflatable convective apparatuses; two are shown in this view, although this configuration is for illustration only. Further, the constructions of the inflatable convective apparatuses are for illustration only; in fact other inflatable convective apparatus constructions may also be adapted for any of the drape embodiments to be described, or any equivalent thereof.

In FIG. 3, the two convective apparatuses are denoted by reference numerals 60 and 70, and each is supported on the inside surface 43 of the clinical garment 22. The figure shows permeable surfaces of the convective apparatuses through which heated air is expelled. The convective apparatus 60 includes an inlet port 61 and two laterally-extending arms 62 extending from sleeve to sleeve of the clinical garment 22. The arms 62 may be folded and retained in the sleeves 53 in the manner explained in the referenced application Ser. No. 11/583,432, filed Oct. 19, 2006, and entitled "Multifunction Warming Device for Perioperative Use". The inlet port 61 is positioned on the side of the convective apparatus 60 that faces the inside surface 43, and it is accessed by way of the flap 29 in the front of the clinical garment 22. The convective apparatus 60 is designed and positioned for delivery of therapeutic warming through a permeable surface 64 to the upper body and arms of a person.

With further reference to FIG. 3, the convective apparatus 70 is disposed between the convective apparatus 60 and the lower hem 47, centered on the longitudinal axis 49. The convective apparatus 70 includes one or more inflatable sections; two are shown for example only. In this regard, a "section" of a convective apparatus is a portion or division of the convective apparatus that may be inflated and operated separately from any other section of the convective apparatus. For example, the convective apparatus 70 has a section 71 and a section 72. The section 71 is inflated and operated separately from the section 72, and the section 72 is inflated and operated separately from the section 71. Each section includes one or more inlet ports; in the illustrated example, the inlet port 74 is in the first section 71, and the inlet port 85 is in the second section 72. Each inlet port 74 and 85 is positioned on the side of the convective apparatus 70 that faces the inside surface 43, with the inlet port 74 accessed by way of the flap 28 in the front of the clinical garment 22 and the inlet port 85 accessed by way of the flap 30 in the front of the clinical garment 22.

With further reference to FIG. 3, the first section 71 of the convective apparatus 70 is adapted for comfort warming by virtue of an average or mean permeability in the surface 79 that is lower than the average or mean permeability in the surface 86 of the second section 72. The lower average permeability of the surface 79 accommodates a lower air pressure entering the first section 71 from a relatively low capacity forced air warming unit, coupled by a smaller-diameter air hose to a smaller inlet port 74. The second section 72 of the convective apparatus 70 is adapted for therapeutic warming by virtue of an average or mean permeability in the surface 86 that is higher than the average or mean permeability in the surface 79 of the first section 71. The higher average permeability of the surface 86 accommodates a higher air pressure entering the second section 72 from a relatively high capacity forced air warming unit, coupled by a larger-diameter air hose to a larger inlet port 27. The convective apparatus 70 is for delivery of comfort warming through the permeable surface 79 of the first section 71 within the space of the clinical garment 22, or delivery of therapeutic warming through the permeable surface 86 of the second section 72 to the thorax and/or lower abdomen of a person.

Each of the convective apparatuses 60 and 70 may be formed by joining two sheets of material with a closed impermeable seam around their peripheries and, in the convective apparatus 70, one or more additional closed impermeable seams to define the separate sections. One of the sheets is relatively impermeable and the other sheet is relatively more permeable to permit airflow therethrough. The sheets are further connected by discontinuous seals or stake points within the closed impermeable seams. The two sheets with which a convective apparatus is formed may be separate from the clinical garment 22, in which case the convective apparatuses are permanently or releasably attached, fixed, or adhered to the inside surface 43 of the clinical garment 22, with their permeable surfaces facing inwardly, toward a patient wearing the device 20. An exemplary construction in this regard is illustrated in FIGS. 1A and 1D and FIGS. 3A-3C of PCT publication WO 2003/086500. Alternately, the convective apparatuses may be formed or constructed integrally with a clinical garment 22 made of relatively impermeable material by attaching relatively permeable sheets to portions of the inside surface of the clinical garment 22. An exemplary construction in this regard is illustrated in FIGS. 1D and 1E and FIGS. 3D-3F of PCT publication WO 2003/086500.

According to the present best mode of construction of the convective warming device thus far described, inflatable convective apparatuses such as 60 and 70 may be formed or assembled separately from the clinical garment 22 and then attached to its inside surface 43 by sewing, gluing, heat sealing, or welding, or any combination of these. For example, each of the convective apparatuses 60 and 70 may be formed by heat sealing two sheets of material together. The convective apparatus 60 may be formed with a laminate sheet comprising a layer of nonwoven material on which a layer of polypropylene is extruded, and a polypropylene film. Apertures may be formed through the laminate sheet and the polypropylene layers are sealed around their peripheries. The polypropylene film is attached to the inside surface of the clinical garment and the nonwoven material faces the patient. A reason for locating the polypropylene film on the inside surface of the clinical garment is to reduce the bulk and stiffness of the convective apparatus 60, thus making the warming device 20 more comfortable to the patient. The sheets used for the convective apparatus 70 may each comprise a layer of spunbond nonwoven material with a polypropylene extrusion coating on one side. This construction is preferred for both sides of the convective apparatus 70. The spunbond material is positioned with its extrusion coated side facing the interior inflatable space of the convective apparatus 70, away from the patient. The polypropylene extrusion makes the nonwoven material air impermeable. That way the air blown into the convective apparatus 70 can be dispersed to the patient by selectively perforating the patient side of the second convective apparatus, which forms the permeable surface of the convective apparatus 70. The side of the convective apparatus 70 that faces the inside surface of the clinical garment 22 is nonwoven, and when the patient slides her or his hands into the hand slits 44, they are in comfortable contact with a soft material.

Figure 4:
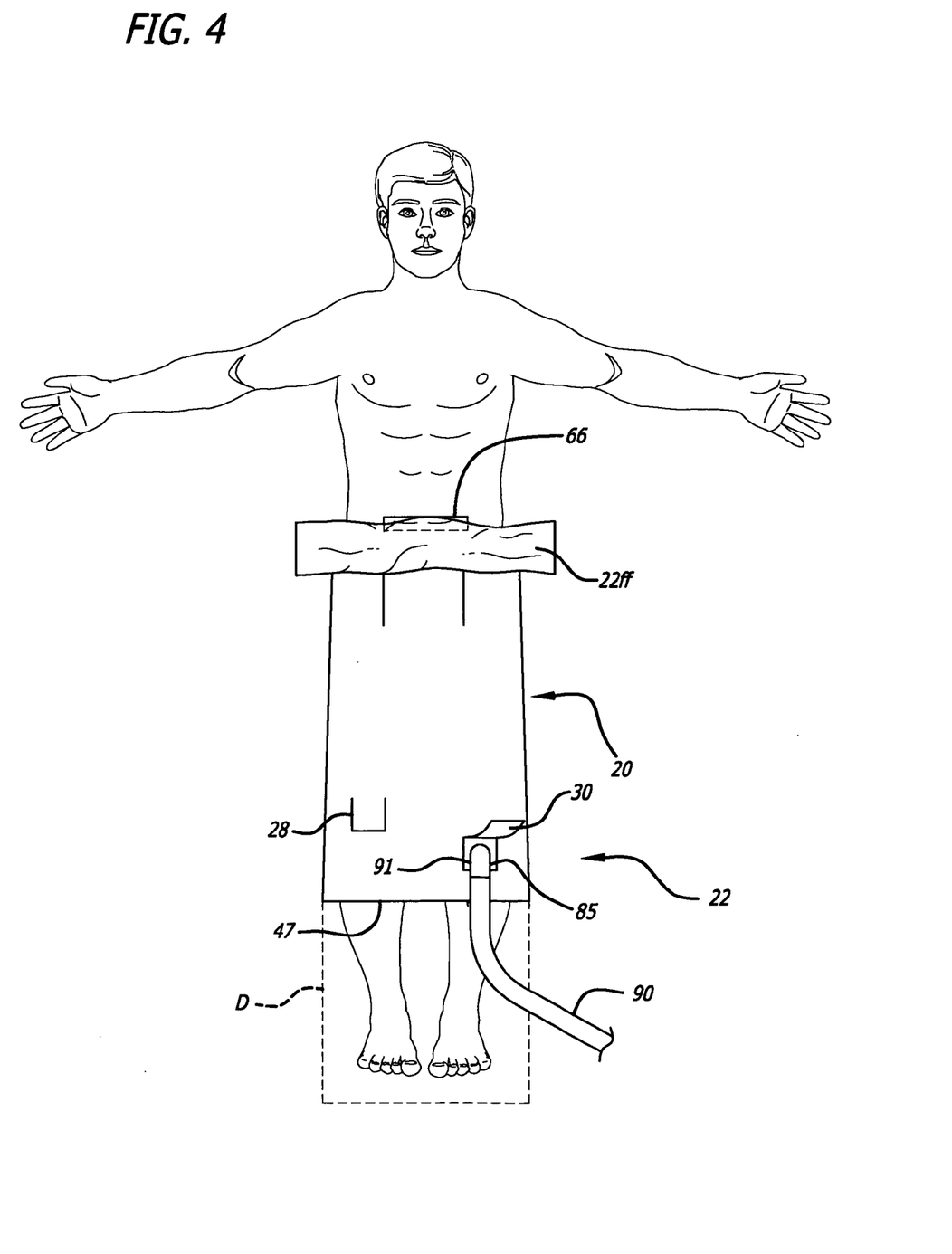
FIG. 4 illustrates preparation and deployment of a convective warming device to therapeutically warm respective body portions of a patient during surgery.

FIG. 4 illustrates how the representative convective warming device 20 is adapted for therapeutic warming using the convective apparatus 70 to warm a patient during surgery. The view is toward the front of the clinical garment 22, from a position above the patient, who is lying on an operating table (not shown), preferably one with cruciate support for the patient's arms. Presuming that at least one inflatable convective apparatus, such as the apparatus 70, is supported in the clinical garment, the convective warming device 20 may be configured as shown in FIG. 4 for therapeutic warming using the section 72 of the convective apparatus 70 by separating the sleeve seams 56 and pulling the sleeves away from the patient's arms. The upper portion 51 of the clinical garment 22 is then pulled down from the patient's upper body and furled or folded at 22ff over the lower portion 55. The clinical garment 22 is loosened about the patient, and the clinical garment 22 may be slid toward the patient's feet if required to clear the surgical site. A double-sided tape 66 may be deployed to adhesively attach the convective warming device 20 to the patient's body. The flap 30 is folded back to expose the inlet port 85 of the second section 72 and a forced air warming unit (not shown) is connected to the inlet port 85 via an air hose 90 and nozzle 91. Thus deployed, the convective apparatus 70 is used to deliver therapeutic warming during surgery on the patient's upper body via the second section 72. After surgery, the clinical garment 22 may be slid toward the patient's upper chest where the upper portion 51 may be unfurled or unfolded from the lower portion 55 toward the patient's shoulders. The sleeves 53 may be pulled upwardly over the patient's shoulders, and the seams 56 may be joined around the shoulders and upper arms to reconfigure the clinical gown 22 to be worn by the patient. Alternatively, the unfurled clinical gown 22 can lie over the patient's upper body to trap warm air about the patient As may be appreciated in FIG. 1, the lower edge, or hem 47 of the clinical garment 22 is positioned just above the knees of the person 11, leaving the person's lower thighs, knees, lower legs, and feet uncovered by the clinical garment 22 and exposed. Further, there are two flaps, 28 and 30, providing access to inlet ports located near the lower edge or hem 47. As seen in FIG. 4, even when the convective warming device is repositioned on a patient prone as on a surgical table, the lower legs and feet of the patient remain uncovered. In this instance, if the air hose 90 were to rest on the patient's uncovered lower left shin when conducting a stream of heated pressurized air, thermal injury to exposed skin could result. Of course, provision of a convective warming device with a clinical garment having a length sufficient to place the lower edge or hem 47 at the lower shins or ankles of a person wearing the gown would mitigate or eliminate the risk of such injury. But this is an impractical solution to the problem of thermal injury, for at least two reasons. First, the longer the clinical garment, the greater the interference with patient mobility when the patient is upright as in FIG. 1. Second, the costs of manufacturing and stocking the great variety of sizes required to fit specific physical configurations of a great variety of users would be prohibitive.

As may be appreciated with reference to FIG. 4, the problem of thermal injury to the lower legs and feet may be solved without excessive length or customization of the clinical garment 22. In order to protect the uncovered skin of the patient from burns caused by contact with a hot air hose, the convective warming device 20 is provided with a drape that can be deployed from the clinical garment 22 to cover the exposed skin. One such deployed drape, indicated by the dashed outline D, extends from the clinical garment 22, past the lower hem 47. Manifestly, the drape D, when deployed from the convective warming device 20 as indicated in FIG. 4, covers the lower legs and feet of the patient. The drape D provides or constitutes a protective layer of material between the skin not covered by the clinical garment 22 and the air hose 90, and that layer mitigates or eliminates the risk of burns resulting from contact between skin and hose while a flow of heated air travels through the hose.

With reference to FIGS. 2 and 4, the drape D is preferably disposed inside of the clinical garment 22, with one end secured therein, where it may be retained in a folded, furled, rolled, or gathered configuration. Then, the drape may be deployed by unfurling it and pulling a free end from inside the clinical garment 22 past the lower edge or hem 47. The drape D is elongate and may be of any length appropriate to the intended application. One advantage of maintaining the drape in a furled configuration is that it can be made in a single standard length sufficient to cover the exposed legs and feet of most patients when prone for surgery, for example, but deployed only when needed, thereby avoiding the reduced mobility and elevated cost associated with long and/or customized clinical garments.

FIGS. 5A, 5B, 6A, and 6B illustrate one example of a drape construction in which the drape is integrated into the structure of an inflatable convective apparatus. However, this example is not meant to limit the provision of a drape for a convective warming apparatus including a clinical garment. In fact, this example, or any equivalent thereof, may be used with any convective warming device constituted of a clinical gown and at least one inflatable convective device supported on an inside surface thereof.

Figure 5A:
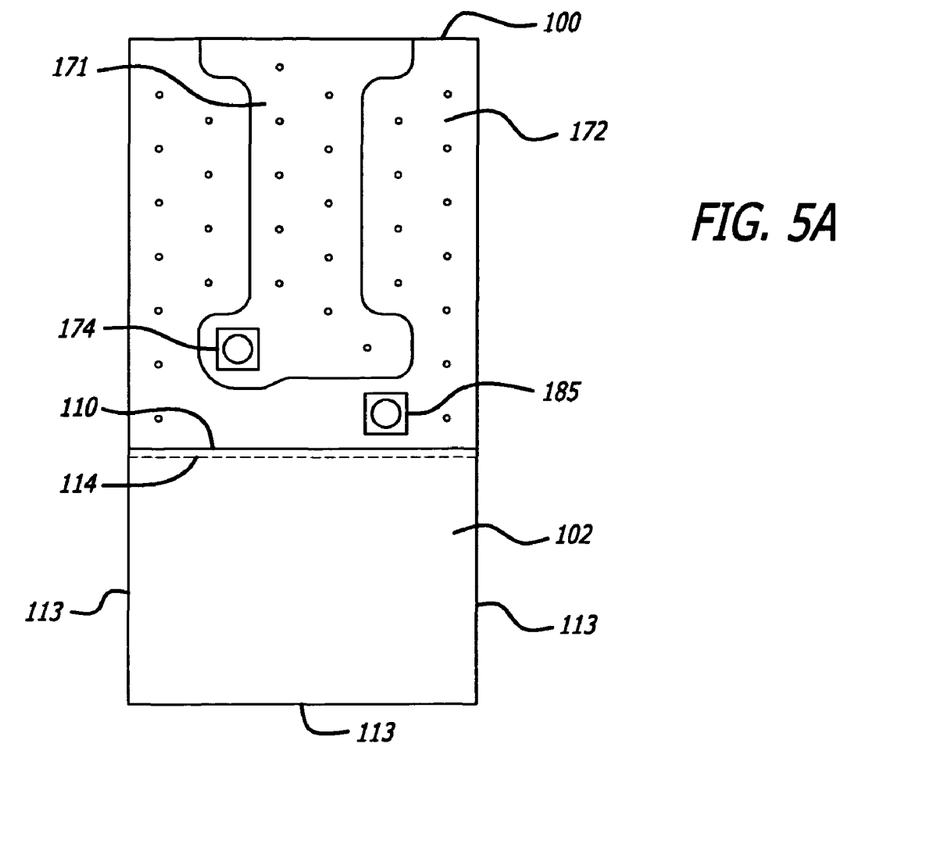
FIGS. 5A and 5B are plan views of an impermeable side of a convective apparatus, showing an embodiment of a drape.
Figure 5B:
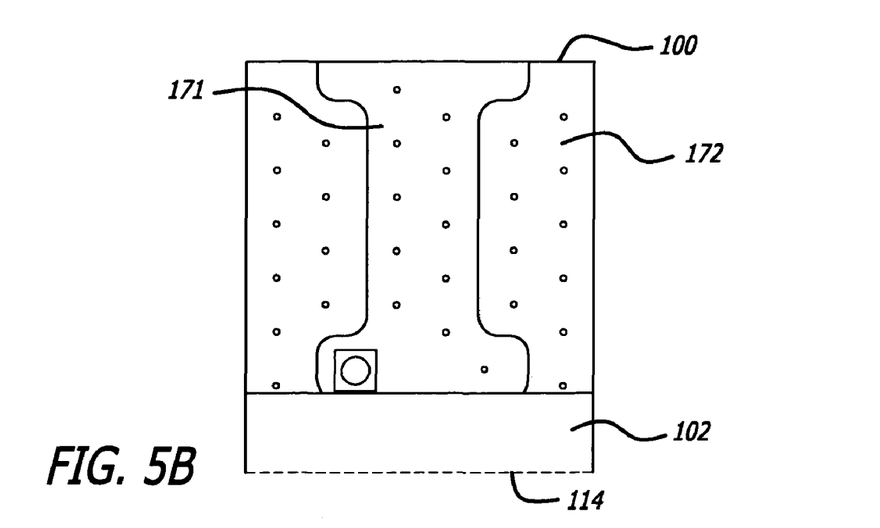
Figures 6A, 7:
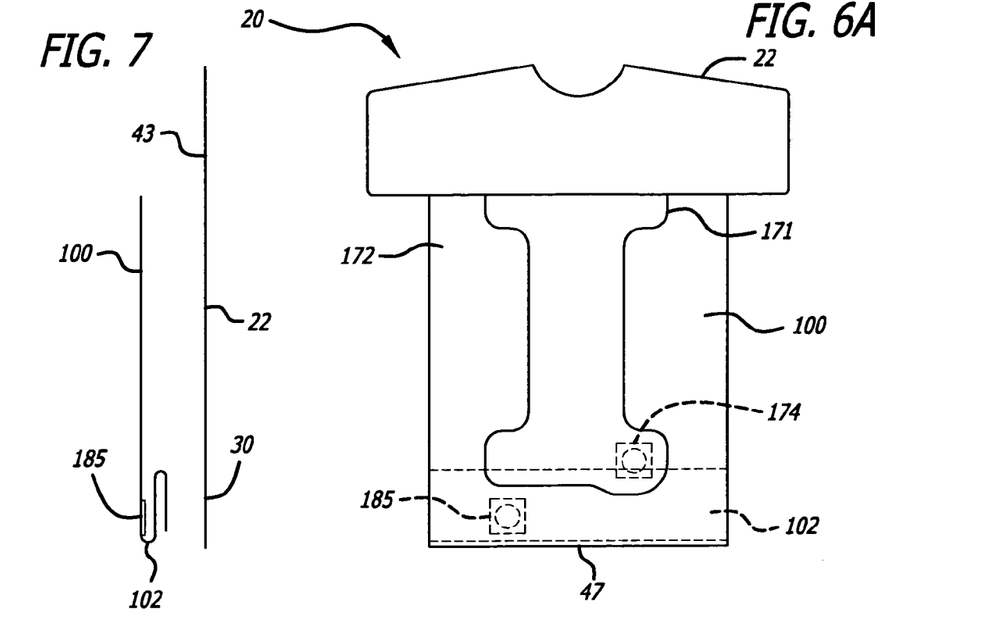
FIGS. 6A and 6B are plan, partially schematic views of a permeable side of the convective apparatus of FIGS. 5A and 5B, in a convective warming device, showing the embodiment of the drape.
FIG. 7 is a side schematic view of the convective warming device of FIGS. 6A and 6B showing the drape folded, furled, rolled, or gathered between the impermeable side and the inside surface of the clinical garment.
Figure 6B:
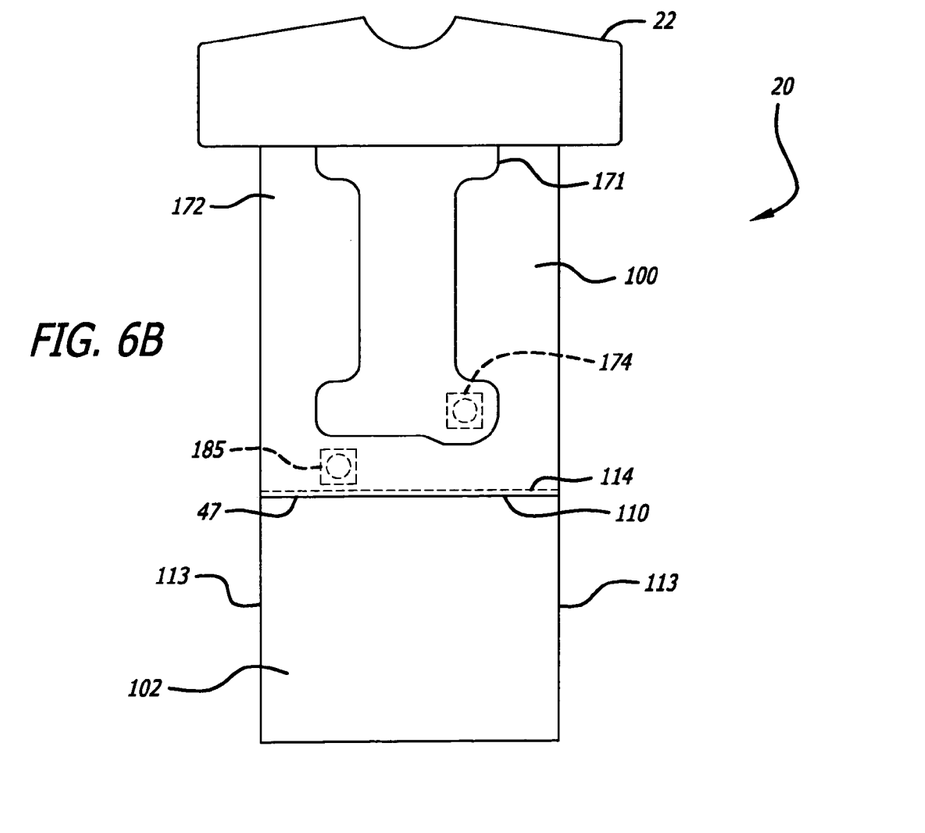

In FIGS. 5A and 5B, the view is toward the impermeable side of a convective apparatus 100 from the inside surface of the clinical garment; in FIGS. 6A and 6B, the view is toward the permeable side of the convective apparatus 100. For this example, with reference to FIGS. 5A and 6B, the convective apparatus 100 is similar in structure and function to the convective apparatus 70 discussed above, and has first and second separately inflatable sections 171 and 172 corresponding to the sections 71 and 72, respectively, of the apparatus 70.

Each of the sections 171 and 172 has one or more inlet ports; for convenience, only inlet ports 174 and 185 are shown.

With reference to FIGS. 5A and 6B in this example, a drape 102 is appended or joined to, or formed at the lower edge of the convective apparatus 100. The drape 102 may have a quadrilateral shape, as shown, although other shapes may also be used. Presuming the convective apparatus is constructed in the same way as the convective apparatus 70, the drape 102 may be formed by an extension of the two sheets with which the convective apparatus is made beyond a seal 110 that defines the lower edge of the convective apparatus 100. The two sheets are joined in the extension by a continuous seal 113 between the two sheets around the periphery of the extension. The seal 110 makes the extension uninflatable by preventing heated pressurized air from flowing into the drape 102. A line 114 of perforations parallel and adjacent to the seal 110 may be provided in the drape 102, extending transversely across the drape 102 from one side of the drape 102 to its opposite side.

As best seen in FIGS. 5B, 6A, and 7, the drape 102 may be folded (or furled, rolled, or gathered) up to the seal 110, and, while folded, releasably retained between the inside surface 43 of the clinical garment 22 and the impermeable side of the convective apparatus 100. A tight clearance between the convective apparatus 100 may be sufficient to retain the folded drape as shown in FIG. 7; double-sided tape (not shown) acting between the folded drape and the inside surface 43 may also be used. Preferably, when folded and retained as shown in FIG. 7, the drape overlies the inlet port 185, blocking access to the port through the flap 30, which serves the section 172 adapted for therapeutic heating. This is a useful safety measure where the covered inlet port serves an inflatable section or apparatus adapted for therapeutic warming. In such a case, the inlet port would be coupled to a large diameter air hose that is hotter during operation than a smaller one serving a comfort warming section or apparatus. Thus, with reference to the example portrayed in FIG. 7, an operator would be prompted to remove the folded drape 102 from between the convective apparatus and the clinical garment in order to gain access to the inlet port 185. The act of gaining access to the inlet port 185 would further prompt the operator to unfurl and deploy the drape 102.

The drape shown in FIGS. 5A, 5B, 6A, 6B, and 7 does not have to be formed integrally with an inflatable convective apparatus; it can be formed separately and attached to either side of an inflatable convective apparatus supported on the inside surface of the clinical garment 22.

FIGS. 8A, 8B, 9A, and 9B illustrate other examples of drape construction in which a drape is attached to or integrated into the structure of a clinical garment. However, these examples are not meant to limit the provision of a drape for a convective warming apparatus including a clinical garment. In fact, any of these other examples, or any equivalent thereof, may be used with any convective warming device constituted of a clinical gown and at least one inflatable convective device supported on an inside surface thereof. Also, in FIGS. 8A, 8B, 9A, and 9B the representative convective warming apparatus 20 as described and illustrated previously is used to provide a basis for explaining and illustrating the structure and use of these other examples of drape construction, but is not intended to limit these examples only to this convective warming device.

Figure 8A:
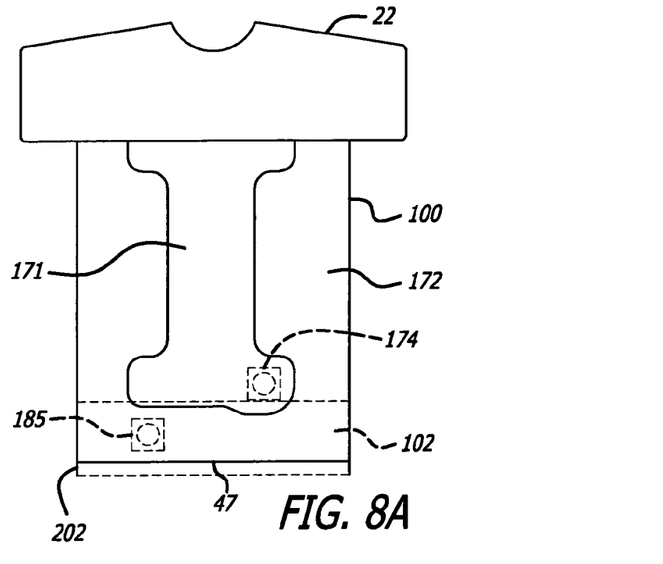
FIGS. 8A and 8B are plan, partially schematic views of a permeable side of a convective apparatus, in a convective warming device, showing another embodiment of the drape.
Figure 8B:
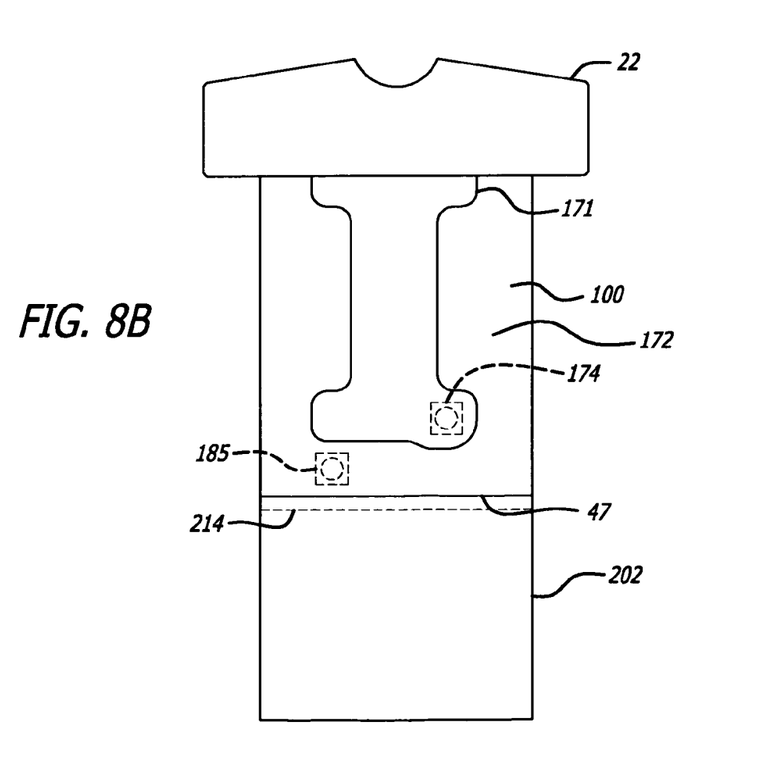

In FIGS. 8A and 8B, the view is toward the permeable side of the convective apparatus 100. For this example, the convective apparatus 100 is as discussed above in connection with FIGS. 5A, 5B, 6A, and 6B, and has first and second separately inflatable sections 171 and 172. A drape 202 is appended or joined to, or formed near the lower edge of the clinical garment 22. Presuming the clinical garment 22 in FIGS. 8A and 8B is constructed in the same way as shown in FIG. 2, the drape 202 may be formed from the same material as the clinical garment 22, or from the same material as the sheets with which an inflatable convective apparatus is assembled, or from any other equivalent material. The drape 202 may have a quadrilateral shape, as shown, although other shapes may also be used. The drape 202 may be attached along one of its sides to the inside surface 43 along the lower hem 47. The drape 202 may be attached by any appropriate mode or mechanism. For example, the drape 202 may be attached to the inside surface 43 by tape, sewing, gluing, heat sealing, or welding, by any combination of these, or by any equivalent. A double-sided tape 187 acting between an edge of the drape 202 and the inside surface 43 may be used to attach the drape 202 to the clinical garment 22, for example. A line of perforations 214 may be provided in the drape 202, extending transversely across the drape 202 from one side of the drape 202 to its opposite side. Preferably the line of perforations 214 would be positioned parallel and adjacent to the lower hem 47 when the drape 202 is attached to the inside surface 43.

Figure 9A:
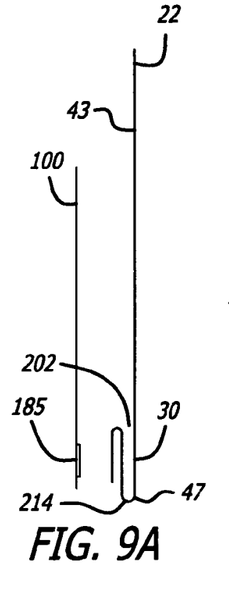
FIGS. 9A and 9B are side schematic views of the convective warming device of FIGS. 8A and 8B showing the drape folded, furled, rolled, or gathered between the impermeable side and the inside surface of the clinical garment

As best seen in FIGS. 8A and 9A, the drape 202 may be folded (or furled, rolled, or gathered) up to and above the lower hem 47, and, while folded, releasably retained between the inside surface 43 of the clinical garment 22 and the impermeable side of the convective apparatus 100. Preferably, when folded and retained as shown in FIG. 9A, the drape 202 overlies the inlet port 185, blocking access to the port through the flap 30 in the same manner and for the same reasons as the drape 102 in FIG. 7.

Of course, as may be inferred from FIGS. 8A, 8B, and 9A, the drape may be formed as a separate element and attached to the outside surface at the front of the clinical garment, and retained there in a folded (or furled, rolled, or gathered) configuration blocking access to an inflation port until unfurled toward and over the lower hem 47. This construction is less desirable because the drape can snag on objects outside the microenvironment or it can be unfurled prematurely by the person wearing the gown.

Figure 9B:
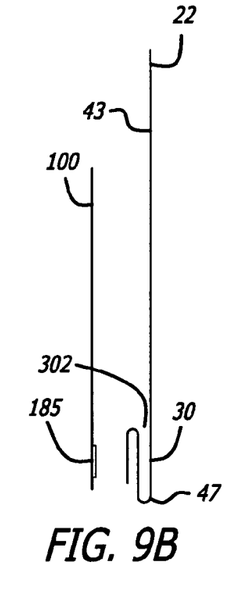

As shown in FIG. 9B a drape 302 may also be formed integrally with the clinical garment 22. In this case, an additional rectangular portion extending beyond the lower hem 47 would be provided in the front of the clinical garment 22 during manufacture. A line of perforations 314 may be provided in the drape 302, extending transversely across the drape 302 from one side of the drape 302 to its opposite side. Preferably the line of perforations 314 would be positioned parallel and adjacent to, or at, the lower hem 47. The additional portion would be folded (or furled, rolled, or gathered) up to and above the lower hem 47, and, while folded, releasably retained between the inside surface 43 of the clinical garment 22 and the impermeable side of the convective apparatus 100. Preferably, when folded and retained as shown in FIG. 9B, the drape 302 overlies the inlet port 185, blocking access to the port through the flap 30 in the same manner and for the same reasons as the drape 102 in FIG. 7.

Presume that the convective warming device 20, with a drape D retained folded (or furled, rolled, or gathered) therein, is disposed on a patient before surgery as shown in FIG. 4. The patient is prone with feet outstretched. The drape D is deployed by rotating it from its retained folded position, pulling the free end of the drape D to unfold the drape D and to extend it past the lower edge or hem 47, and pulling the free end of the drape D down and over a patient's feet. When the drape D is thus deployed, the operator connects an air hose to the inlet port 85 such that at least a portion of the air hose contacts or rests on the drape D over the patient's lower legs and/or feet. This can be seen in FIG. 4, where the air hose 90 contacts the drape D over the patient's lower left shin. The forced air warming unit to which the air hose is connected is turned on, the convective apparatus is inflated, and the patient is warmed. When the warming is finished, at a time after the drape D has been deployed for use, the forced air warming unit is turned off, and the air hose is disconnected from the inlet port. The drape D may then be folded back into the clinical garment 22 or it may be removed from the convective warming device 20. For example, if the drape D has a line of perforations near or at the lower hem 47, it can be detached by tearing along the line.

Of course, the just-described examples are not intended, nor should they be understood, to limit the possible ways a drape can be provided with and deployed from the clinical garment of a convective warming device. The drape can be formed integrally with an element of the convective warming device; or, it can be formed as a separate element and attached to an element of the convective warming device. Although the drape is described as being uninflatable, it may be useful to provide a drape that is capable of some degree of inflation.

I claim:

1. A convective warming device, comprising:
   a clinical garment having an inside surface and a lower hem;
   an inflatable convective apparatus supported on the inside surface; and
   a drape extendable from inside the clinical garment past the lower hem.

2. The convective warming device of claim 1, the drape including an extension of the inflatable convective apparatus.

3. The convective warming device of claim 2, wherein the drape is uninflatable.

4. The convective warming device of claim 2, further including means for separating the extension from the inflatable convective apparatus.

5. The convective warming device of claim 2, further including a line of perforations in the extension near the inflatable convective apparatus.

6. The convective warming device of claim 2, wherein the drape is in a folded configuration releasably held between the convective apparatus and the inside surface.

7. The convective warming device of claim 1, the drape being attached to the inflatable convective apparatus.

8. The convective warming device of claim 7, further including a line of perforations in the drape near the inflatable convective apparatus.

9. The convective warming device of claim 7, the drape being releasably retained in a folded configuration between the inflatable convective apparatus and the inside surface.

10. The convective warming device of claim 1, the drape being attached to the inside surface of the clinical garment.

11. The convective warming device of claim 10, further including a line of perforations in the drape.

12. The convective warming device of claim 10, the drape being releasably retained in a folded configuration between the inflatable convective apparatus and the inside surface.

13. The convective warming device of claim 1, the drape being an extension of a portion of the clinical garment past the lower hem.

14. The convective warming device of claim 13, further including a line of perforations in the drape.

15. The convective warming device of claim 13, the drape being releasably retained in a folded configuration between the inflatable convective apparatus and the inside surface.

16. A convective warming device, comprising:
    a clinical garment having an inside surface and a lower hem;
    an inflatable convective apparatus supported on the inside surface;
    at least one inlet port in the inflatable convective apparatus, near the lower hem, for receiving an air hose nozzle; and
    a drape extendable from the clinical garment past the lower hem.

17. The convective warming device of claim 16, wherein the drape is extendable from inside the clinical garment.

18. The convective warming device of claim 17, the drape being releasably retained in a folded configuration between the inflatable convective apparatus and the inside surface.

19. The convective apparatus of claim 18, wherein the folded configuration covers the at least one inlet port.

20. The convective warming device of claim 16, wherein the drape is formed on an edge of the inflatable convective device.

21. The convective warming device of claim 16, wherein the drape is attached to the inflatable convective device.

22. The convective warming device of claim 16, wherein the drape is attached to the inside surface.

23. The convective warming device of claim 16, wherein the drape is formed as an extension of a portion of the clinical garment past the lower hem.

24. A method of operating a convective warming apparatus including a clinical garment with an inside surface and a lower hem, an inflatable convective apparatus supported on the inside surface, and a drape attached to the convective warming apparatus, comprising:
    disposing the clinical garment on a person; and
    deploying the drape over at least the person's legs.

25. The method of claim 24, wherein the drape is attached inside the clinical garment and deploying the drape includes deploying the drape from inside the clinical garment, past the lower hem and over at least the person's legs.

26. A method of operating a convective warming apparatus including a clinical garment with an inside surface and a lower hem, an inflatable convective apparatus supported on the inside surface, an inlet port in the convective apparatus, and an elongate drape having one end secured inside the clinical garment and an opposing free end, comprising:
    folding the drape into the clinical garment, toward the secured end;
    disposing the clinical garment on a person;
    unfolding the drape; and
    moving the free end past the lower hem, over at least the person's legs.

27. The method of claim 26, further including, after folding, retaining the folded drape between the inside surface and the inflatable convective apparatus.

28. The method of claim 26, further including:
    connecting an air hose to the inlet port;
    resting the air hose on the drape; and
    providing a flow of heated air through the air hose.

29. The method of claim 28, further including:
    ceasing the airflow;
    disconnecting the air hose from the inlet port; and
    separating the drape from the convective warming apparatus.

* * * * *

UNITED STATES PATENT AND TRADEMARK OFFICE
CERTIFICATE OF CORRECTION

| | | |
|---|---|---|
| PATENT NO. | : 7,862,599 B2 | Page 1 of 1 |
| APPLICATION NO. | : 11/656777 | |
| DATED | : January 4, 2011 | |
| INVENTOR(S) | : Thomas P. Anderon et al. | |

It is certified that error appears in the above-identified patent and that said Letters Patent is hereby corrected as shown below:

Column 3
Line 61, after "garment" insert -- . --.

Column 7
Line 61, after "patient" insert -- . --.

Signed and Sealed this

Eleventh Day of September, 2012

David J. Kappos
*Director of the United States Patent and Trademark Office*